(12) United States Patent
Boch et al.

(10) Patent No.: US 6,984,395 B2
(45) Date of Patent: Jan. 10, 2006

(54) DRUG DELIVERY SYSTEM FOR HYDROPHOBIC DRUGS

(75) Inventors: Ronald Erwin Boch, Vancouver (CA); Dev Mitra Ranji Singh, Surrey (CA); Iman Karmadi, Vancouver (CA)

(73) Assignee: QLT, Inc., Vancouver (CA)

( * ) Notice: Subject to any disclaimer, the term of this patent is extended or adjusted under 35 U.S.C. 154(b) by 0 days.

(21) Appl. No.: 09/833,406

(22) Filed: Apr. 11, 2001

(65) Prior Publication Data

US 2002/0156062 A1    Oct. 24, 2002

(51) Int. Cl.
*A61K 9/127*    (2006.01)

(52) U.S. Cl. ............... 424/450; 424/6.1; 514/410; 514/937

(58) Field of Classification Search .......... 424/450, 424/1.21, 9.321, 9.51, 9.6, 9.61; 428/402.2; 514/410, 937
See application file for complete search history.

(56) References Cited

U.S. PATENT DOCUMENTS

| | | | |
|---|---|---|---|
| 4,512,762 A | 4/1985 | Spears | 604/21 |
| 4,577,636 A | 3/1986 | Spears | 128/654 |
| 4,649,151 A | 3/1987 | Dougherty et al. | 514/410 |
| 4,753,788 A * | 6/1988 | Gamble | 424/1.21 |
| 4,753,958 A | 6/1988 | Weinstein et al. | 514/410 |
| 4,776,991 A | 10/1988 | Farmer et al. | 264/4.3 |
| 4,866,168 A | 9/1989 | Dougherty et al. | 540/145 |
| 4,883,790 A | 11/1989 | Levy et al. | 540/145 |
| 4,889,129 A | 12/1989 | Dougherty et al. | 128/664 |
| 4,920,143 A | 4/1990 | Levy et al. | 514/410 |
| 4,932,934 A | 6/1990 | Dougherty et al. | 604/21 |
| 4,946,683 A * | 8/1990 | Forssen | 424/422 |
| 5,010,073 A | 4/1991 | Kappas et al. | 514/185 |
| 5,095,030 A | 3/1992 | Levy et al. | 514/410 |
| 5,096,629 A | 3/1992 | Nanba et al. | 264/4.1 |
| 5,171,749 A | 12/1992 | Levy et al. | 514/410 |
| 5,257,970 A | 11/1993 | Dougherty | 604/20 |
| 5,270,053 A | 12/1993 | Schneider et al. | 424/450 |
| 5,320,906 A * | 6/1994 | Eley et al. | 428/402.2 |
| 5,329,029 A * | 7/1994 | Wan | |
| 5,389,378 A * | 2/1995 | Madden | |
| 5,435,989 A * | 7/1995 | Presant et al. | 424/1.21 |
| 5,707,608 A | 1/1998 | Liu | 424/9.61 |
| 5,879,703 A * | 3/1999 | Fountain | 424/450 |
| 5,880,145 A | 3/1999 | Sternberg et al. | 514/410 |
| 5,885,557 A * | 3/1999 | Lentini | |
| 5,922,355 A | 7/1999 | Parikh et al. | 424/489 |
| 5,929,105 A | 7/1999 | Sternberg et al. | 514/410 |
| 5,990,149 A | 11/1999 | Sternberg et al. | 514/410 |
| 6,074,666 A | 6/2000 | Desai et al. | 424/450 |
| 6,153,639 A | 11/2000 | Sternberg et al. | 514/410 |

(Continued)

FOREIGN PATENT DOCUMENTS

WO    WO 97/04746    2/1997

(Continued)

OTHER PUBLICATIONS

Brodin et al., Acta Pharm. Suec. (1982) 19:267-284.

(Continued)

*Primary Examiner*—Gollamudi S. Kishore
(74) *Attorney, Agent, or Firm*—Morrison & Foerster LLP

(57) ABSTRACT

Compositions comprising microaggregates containing hydrophobic drugs, as well as methods for their production, are described. Such microaggregates may include micelle structures or combinations thereof with liposomes, and constitute an effective delivery vehicle for a hydrophobic agent. Methods for microaggregate production include the use of preferred lipid compounds and processing conditions favoring the production of small aggregates for improved filter sterilization.

15 Claims, 1 Drawing Sheet

U.S. PATENT DOCUMENTS 6,375,930 B2 * 4/2002 Young

FOREIGN PATENT DOCUMENTS

| WO | WO 98/48621 | 11/1998 |
| WO | WO 00/34763 | 6/2000 |
| WO | WO 01/85213 | 11/2001 |

OTHER PUBLICATIONS

Cozzani et al., In Porphyrins in Tumor Phototherapy, 177-183, Plenum Press (Andreoni et al. eds. 1984).
Diamond et al., Lancet, (1972) 2:1175-77.
Dougherty et al., "The Science of Photo Medicine", 625-38 (Regan et al. eds. 1982).
Dougherty et al., "Cancer: Principles and Practice of Oncology", 1836-44 (DeVita Jr. et al. eds. 1982).
Fung et al., Biomater. Artif. Cells. Artif. Organs (1988) 16:439 et. seq.
Johnson et al., Proc. Photodymanic Therapy: Mechanisms II, Proc. SPIE-Int. Soc. Opt. Eng., (1990) 1203:266-80.
Jori et al., Br. J. Cancer, (1983) 48:307-309.
Lasic, Nature (1992) 355:379-380.
Moon and Giddings, J. Pharm. & Biomed. Analysis, (1993) 11:911-20.
Lipson et al., J. Natl. Cancer Inst., (1961) 26:1-8.
Madden et al., Biochemistry (1988) 27:8724-8730.
Milanesi, Int. J. Radiat. Biol. (1989) 55:59-69.
Redmond and Gamlin, Photochem. Photobiol. (1999) 70(4): 391-475.
Ricchelli, New Directions in Photodynamic Therapy (1987) 847:101-106.
Supersaxo et al., Pharm. Res. (1991) 8:1286-1291.
Weishaupt et al., Cancer Research (1976) 36:2326-29.
Yokoyama et al., Cancer Res. (1991) 51:3229-3236.
Zhou et al., Photochemistry and Photobiology, (1988) 48: 487-92.
Tatman, D., et al., "Carotenohematoporphyrins as Tumor—Imaging Dyes. Synthesis and In Vitro Photophysical Characterization" Photochemistry and Photobiology 68 (4):459-466 (1998).

* cited by examiner

DRUG DELIVERY SYSTEM FOR HYDROPHOBIC DRUGS

FIELD OF THE INVENTION

The invention relates to water soluble microaggregates of water insoluble, poorly soluble or otherwise hydrophobic agents and phospholipids or lipids which may be used pharmaceutically, agriculturally or industrially. These microaggregate compositions may be used to deliver hydrophobic drugs as a pharmaceutical formulation, hydrophobic compounds related to plant growth as an agricultural product, and hydrophobic reagents as an industrial material. Moreover, the microaggregates of the invention comprise combinations of natural and/or synthetic phospholipids which permit aggregation with the hydrophobic agents to result in micelles, liposomes, and mixtures thereof. Particular combinations of hydrophobic agents and phospholipids or lipids produce microaggregates that are effective delivery vehicles of said compounds.

Additionally, the invention relates to processes for the production of said microaggregates as delivery systems. These processes include microfluidization (liquid jet milling), high shear mixing, and sonication. Particular processes, involving the use of specific combinations of hydrophobic agents and phospholipids or lipids, permit the large scale preparation of effective delivery vehicles for hydrophobic agents.

DESCRIPTION OF THE RELATED ART

The existence of a wide array of active hydrophobic or otherwise water insoluble agents is known in the art. Similarly there is awareness of the need to deliver such active agents to water based or otherwise aqueous environments. As such, multiple systems have been development as delivery vehicles for such agents. These include the use of organic solvents, aqueous/detergent mixtures, aqueous/organic solvent mixtures (such as co-solvents), emulsions, liposomes, and micelles. Each of these systems, however, have limitations arising from considerations such as the degree of water insolubility and the environment into which delivery is desired.

An example of hydrophobic agents in liposomes is taught by Farmer et al., U.S. Pat. No. 4,776,991, which discloses the large-scale encapsulation of hemoglobin. Kappas et al., U.S. Pat. No. 5,010,073, discloses the preparation of liposomes containing a metalloporphyrin with egg phosphatidyl choline ("EPC") being used as the lipid. Schneider et al., U.S. Pat. No. 5,270,053, discloses liposome formulations said to be free of solid particles and larger lipid aggregates. Parikh et al., U.S. Pat. No. 5,922,355, disclose microparticles comprising insoluble substances. Lasic (Nature, Vol. 355, pp. 379–380, (1992)) describes the use of mixed micelles comprising a drug agent and biological lipids.

Similarly, micelles have also been used to deliver medications to patients, (Brodin et al., Acta Pharm. Suec. 19 267–284 (1982)) and micelles have been used as drug carriers and for targeted drug delivery, (Supersaxo et al., Pharm. Res. 8:1286–1291 (1991)), including cancer medications, (Fung et al., Biomater. Artif. Cells. Artif. Organs 16: 439 et. seq. (1988); and Yokoyama et al., Cancer Res. 51: 3229–3236 (1991)).

Hydrophobic agents of great interest include the polypyrrolic macrocycle based photosensitizing compounds and, in particular green porphyrins such as BPD-MA (benzoporphyrin derivative monoacid ring A, also know by its generic name, verteporfin). These compounds have been known for some time to be useful, when combined with light, for the treatment and diagnosis of a variety of conditions, including tumors, angiogenesis and neovasculature, restenosis and atherosclerotic plaques, and rheumatoid arthritis. The porphyrins have a natural tendency to "localize" in malignant or proliferating tissue, where they absorb light at certain wavelengths when irradiated. The absorbed light may result in a cytotoxic effect in the cells, and neighboring cells, into which the porphyrins have localized. (See, e.g., Diamond et al., Lancet, 2:1175–77 (1972); Dougherty et al., "The Science of Photo Medicine", 625–38 (Regan et al. eds. 1982); and Dougherty et al., "Cancer: Principles and Practice of Oncology", 1836–44 (DeVita Jr. et al. eds. 1982)). It has been postulated that the cytotoxic effect of porphyrins is due to the formation of singlet oxygen when exposed to light (Weishaupt et al., Cancer Research, 36:2326–29 (1976)).

Accordingly, preparations containing the porphyrins are useful in the diagnosis and the detection of important cells and tissue (see, e.g. "Porphyrin Photosensitization", Plenum Press (Kessel et al. eds. 1983)), such as those related to tumors, growing vasculature, arterial blockage and autoimmunity. Similar photosensitizers have been used in the detection and treatment of atherosclerotic plaques, as disclosed in U.S. Pat. Nos. 4,512,762 and 4,577,636. In addition to systemic use for the diagnosis and treatment of various conditions, the porphyrins can be used in a variety of other therapeutic applications. Porphyrin compounds have been used topically to treat various skin diseases, as disclosed in U.S. Pat. No. 4,753,958.

A number of porphyrin photosensitizer preparations have been disclosed for therapeutic applications. A photosensitizer preparation widely used during the early days of photodynamic therapy both for detection and treatment was a crude derivative of hematoporphyrin, also called hematoporphyrin derivative ("HPD") or Lipson derivative, prepared as described by Lipson et al., J. Natl. Cancer Inst., 26:1–8 (1961). A purified form of the active component(s) of HPD was prepared by Dougherty and co-workers by adjustment of the pH to cause aggregation, followed by recovery of the aggregate, as disclosed in U.S. Pat. Nos. 4,649,151; 4,866,168; 4,889,129; and 4,932,934. A purified form of this product is being used clinically under the trademark Photofrin® (Axcan Pharmaceuticals), which is porfimer sodium.

Of particular interest is a group of modified porphyrins, known as "green porphyrins" (Gp), having one or more light absorption maxima between about 670–780 nm. These Gp compounds have been shown to confer cytotoxicity against target cells at concentrations lower than those required for hematoporphyrin or HPD. Gp compounds can be obtained using Diels-Alder reactions of protoporphyrin with various acetylene derivatives under the appropriate conditions. Preferred forms of Gp are the hydro-monobenzoporphyrin derivatives ("BPD's") as well as BPD-MA, EA6 and B3 in particular. The preparation and use of the Gp and BPD compounds are disclosed in U.S. Pat. Nos. 4,920,143, 4,883, 790 and 5,095,030, hereby incorporated by reference into the disclosure of the present application. The preparation and uses of EA6 and B3 are disclosed in U.S. Pat. Nos. 6,153,639 and 5,990,149 respectively, also hereby incorporated by reference.

Many desirable hydro-monobenzoporphyrin photosensitizers, such as BPD-MA, are not only insoluble in water at physiological pH's, but are also insoluble in (1) pharmaceutically acceptable aqueous-organic co-solvents, (2) aqueous polymeric solutions, and (3) surfactant/micellar solutions. It has recently been shown that the encapsulation of certain drugs in liposomes, prior to administration, has a marked effect on the pharmacokinetics, tissue distribution, metabolism and efficacy of the therapeutic agent. In an effort to increase the tumor selectivity of porphyrin photosensitizers, porphyrin compounds have been incorporated into unilamellar liposomes, resulting in a larger accumulation and a more prolonged retention of the photosensitizer by both cultured malignant cells and in experimental tumors in vivo. Jori et al., *Br. J. Cancer,* 48:307–309 (1983); Cozzani et al., *In Porphyrins in Tumor Phototherapy,* 177–183, Plenum Press (Andreoni et al. eds. 1984). This more efficient targeting of tumor tissues by liposome-associated porphyrins may be due in part to the specific delivery of phospholipid vesicles to serum lipoproteins, which have been shown to interact preferentially with hyperproliferative tissue, such as tumors, through receptor-mediated endocytosis. In this manner, the selectivity of porphyrin uptake by tumors has been increased, as compared with photosensitizers dissolved in aqueous solution. See Zhou et al., *Photochemistry and Photobiology,* 48:487–92 (1988).

Accordingly, hematoporphyrin and hematoporphyrin dimethyl esters have been formulated in unilamellar vesicles of dipalmitoyl phosphatidyl choline (DPPC) and liposomes of dimyristoyl (DMPC) and distearoyl phosphatidyl choline (DSPC). Zhou et al., supra; Ricchelli, *New Directions in Photodynamic Therapy,* 847:101–106 (1987); Milanesi, *Int. J. Radiat. Biol.,* 55:59–69 (1989). Similarly, HP, porfimer sodium, and tetrabenzoporphyrins have been formulated in liposomes composed of egg phosphatidyl choline (EPC). Johnson et al., *Proc. Photodynamic Therapy: Mechanisms II,* Proc. SPIE-Int. Soc. Opt. Eng., 1203:266–80 (1990). Additionally, BPD-MA can be "solubilized" at a concentration of about 2.0 mg/ml in aqueous solution using an appropriate mixture of phospholipids to form encapsulating liposomes. Such "solubilized" liposome compositions are suitable for parenteral administration.

Further, freeze-dried pharmaceutical formulations comprising a porphyrin photosensitizer, a disaccharide or polysaccharide, and one or more phospholipids (such as EPG and DMPC) have been made. These formulations form liposomes containing an effective amount of porphyrin photosensitizer upon reconstitution with a suitable aqueous vehicle and are described in Desai et al., U.S. Pat. No. 6,074,666, which is incorporated by reference. Methods for the large-scale production of DMPC/EPG liposomes containing a photosensitizer are disclosed in U.S. Pat. No. 5,707,608, which is incorporated by reference as if fully set forth.

It has been a challenge to find suitable pharmaceutical formulations for hydrophobic polypyrrolic macrocycle based photosensitizers that can be filter sterilized and freeze dried, and can also be rapidly reconstituted in an aqueous medium prior to administration, while retaining a small particle size after rehydration. Photosensitive compunds such as verteporfin (BPD-MA) and QLT 0074 (EA6) must be lyophilized for storage, because they are labile in an aqueous environment.

SUMMARY OF THE INVENTION

The present invention provides a phospholipid composition into which hydrophobic photosensitizers may be incorporated that could be processed into a stable liposome product small enough to be sterile filtered, lyophilized for storage, and would rapidly dissolve in an aqueous medium for administration, while maintaining the small particle size. It was initially believed that the phospholipids of choice would contain only saturated lipids, because saturated lipids are more stable, eliminating the need for anti-oxidants in pharmaceutical preparation. The initial attempts for a composition using saturated phospholipids failed. Surprisingly, it was found that the presence of at least some unsaturated lipid in the composition was essential for a stable, robust product that would survive the lyophilization process intact. Additionally, it was found that the presence of at least some phospholipids having negatively charged polar headgroups contributed to the stability of the composition.

Another totally unexpected finding was that bilayer forming phospholipids comprising a proportion of unsaturated charged lipids were capable of assuming a micellular structure (with or without the incorporation of a hydrophobic molecule) if the material was subjected to a high energy process, such as microfluidization. The production of micelles from bilayer forming lipids is believed to be completely novel, and would not have been predicted from the literature on bilayer forming lipids.

The present invention relates to microaggregates of lipids and hydrophobic agents. In particular, the microaggregates are produced by combining phospholipids and active hydrophobic compounds. Such compositions may be used in any therapeutic, agricultural or industrial setting, and as such, they are delivery vehicles for the active hydrophobic agents. Preferably, the microaggregates comprise micelles and/or small liposomes containing a therapeutically acceptable amount of a hydro-monobenzoporphyrin photosensitizer. The lipids used for microaggregate production comprise unsaturated lipids, and may be stabilized by the presence of antioxidants. Preferably, the microaggregates comprise a mixture of saturated and unsaturated lipids. Preferably, the microaggregates comprise phospholipids having a headgroup that is negatively charged over the pH range of 5–7. Alternatively, the microaggregates may comprise both micelles and liposomes produced from, or containing, the same combination of phospholipids.

The present invention also relates to methods of producing microaggregates comprising lipids and hydrophobic agents. It has been discovered that with appropriate selection of lipids, salt conditions, temperature, and size reduction process, microaggregates comprising differing amounts of liposomes and micelles can be produced. Appropriately selected combinations of lipids, low salt conditions, and a high energy process such as microfluidization can result in the production predominantly micelle comprising microaggregate compositions.

The microaggregates of the invention provide nearly 100% incorporation of a hydrophobic agent such as a hydro-monobenzoporphyrin photosensitizer, which can be expensive and usually requires a complicated synthetic procedure to produce. Thus, there is little reworking necessary and very little waste of the photosensitizer. In addition, due to their small particle size, the present microaggregates exhibit the improved filterability important in producing large quantities of photosensitizer-containing delivery vehicles. Further, the microaggregates retain their small size following lyophilization and reconstituion with an aqueous medium for pharmaceutical delivery. Such photosensitizing microaggregate compositions are useful in mediating the destruction of unwanted cells or tissues or other undesirable materials, or to detect their presence through fluorescence, upon appropriate irradiation. Particularly preferred hydro-monobenzoporphyrin photosensitizers used in the practice of this invention include those having one or more light absorption maxima in the range of 670–780 nm.

BRIEF DESCRIPTION OF THE DRAWINGS

Other objects, features, and advantages are evident from the following descriptions of the various embodiments and the accompanying drawings, in which.

DETAILED DESCRIPTION OF THE INVENTION

Figure 1:
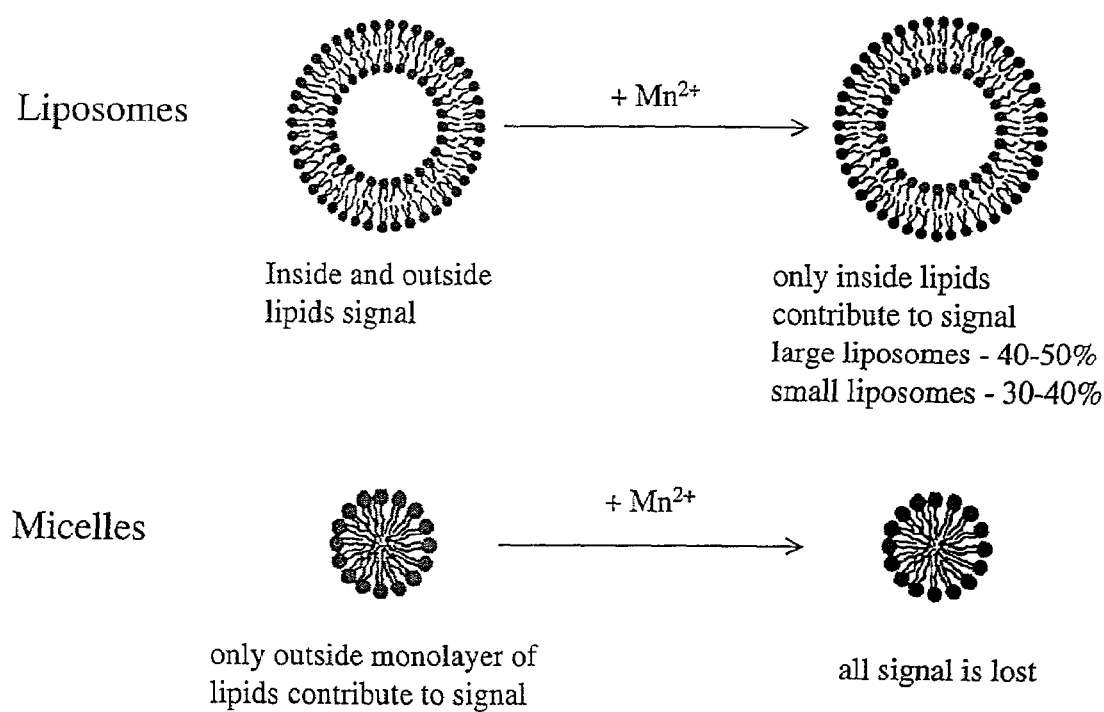
FIG. 1 is a graphic representation of $^{31}$P-NMR of liposomes and micelles in the presence of $Mn^{2+}$.

The invention relates to water soluble microaggregates (MA) of hydrophobic agents and phospholipids or lipids. Water soluble microaggregates are those which are miscible in water or other aqueous solutions. Microaggregates refer to submicron size aggregates of regular or irregular, and spherical or non-spherical shape. For aggregates of roughly spherical shape, the approximate diameters are less than one micrometer. For significantly non-spherical aggregates, the approximate diameter of the aggregate when rotating is less than one micrometer. Aggregates refer to compositions comprising any aggregated complex of constituent molecules. Hydrophobic agents refer to those which are poorly soluble (less than 5 mg/ml water) or insoluble in water or other aqueous solutions.

Hydrophobic agents for formulation into the MA of the invention include any that may be used pharmaceutically, agriculturally or industrially. These include biologically active, or otherwise useful, molecules, pharmaceuticals, imaging agents, and manufacturing reagents as well as precursors and prodrugs of such substances. Preferred hydrophobic agents are those with biological activity or other utility in humans and other living organisms. These include agents that are therapeutics in medicine, ingredients in cosmetics, and pesticides and herbicides in agriculture. Examples of such agents include agonists and antagonists, analgesic and anti-inflammatory agents, anesthetics, antiadrenergic and antarrhythmics, antibiotics, anticholinergic and cholinomimetic agents, anticonvulsant agents, antidepressants, anti-epileptics, antifungal and antiviral agents, antihypertensive agents, antimuscarinic and muscarinic agents, antineoplastic agents, antipsychotic agents, anxiolytics, hormones, hypnotics and sedatives, immunosuppressive and immunoactive agents, neuroleptic agents, neuron blocking agents, and nutrients. Particularly preferred agents include porphyrin photosensitizers such as "green porphyrins" such as BPD-MA, EA6 and B3. Generally, any polypyrrolic macrocyclic photosensitive compound that is hydrophobic can be used in the invention.

Examples of these and other photosensitizers for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol*, 70(4):391–475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis( 1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis( 1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis( 1,1-dimethylethyl)selenopyran-4-ylidene]-3-propenyl]-; selenopyrilium percheorate, 2,6-bis( 1,1-dimethyl-ethyl)-4-[1-[2,6-bis(1,1-dimethyl-ethyl)-4-[1-[2,6-bis( 1,1-dimethyl-ethyl)telluropyran-4-ylidene]-3-propenyl]-; selenopyrilium hexofluoro phosphate, 2,6-bis( 1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene] -4-(2-pentenyl)]-; telluropyrilium tetrafluoroborate, 2,6-bis(1,1-dimethylethyl)-4-[ 1-[2,6-bis(1,1-dimethyl-ethyl)-telluropyran-4-ylidene]-3-propenyl]-; telluropyrilium hexofluoro phosphate, 2,6-bis(1,1-dimethylethyl)-4-[1-[2,6-bis(1,1-dimethyl-ethyl)telluropyran-4-ylidene]-3-propenyl]-; telluropyrilium hexofluoro phosphate, 2,6-bis( 1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethylethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl)bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethyl-ester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate;$13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$ deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcournarin; 5,7-dimethoxy-3-(1-naphthoyl) coumarin; 6-methylcoumarin; 2H-selenolo[3,2-g][1]benzopyran-2-one; 2H-selenolo[3,2-g][1]benzothiopyran-2-one; 7H-selenolo[ 3,2-g][1]benzoseleno-pyran-7-one; 7H-selenopyrano[3,2-f][1]benzofuran-7-one; 7H-selenopyrano[3,2-f][1]benzo-thiophene-7-one; 2H-thienol[3,2-g][1] benzopyran-2-one; 7H-thienol[3,2-g][1] benzothiopyran-7-one; 7H-thiopyrano[3,2-f] [1] benzofuiran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2–18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-( 4-hydroxy-cyclohexano)-buckminsterfullerene; [1-methyl-succinate-4-methyl-cyclohexadiene-2,3 ]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-( 1,1-dimethylethyl)tetranaphtho(2,3-b:2',3'-g:2"3"-1:2'"3'"-q)porphyrazine; zinc (II) 2-(3-pyridyloxy)benzo[b]-10,19,28-tri(1,1-dimethylethyl)trinaphtho[2',3'-g:2"3"1::2'",3'"-q] porphyrazine; zinc (II) 2,18-bis-(3-pyridyloxy)dibenzo[b,1]-10,26-di(1,1-dimethyl-ethyl)dinaphtho[ 2',3'-g:2",3'"-q] porphyrazine; zinc (II) 2,9-bis-(3-pyridyloxy)dibenzo[ b,g]-17,26-di(1,1-dimethyl-ethyl)dinaphtho[2",3"-1:2'",3'"-q] porphyrazine; zinc (II) 2,9,16-tris-(3-pyridyloxy) tribenzo [b,g,1]-24=(1,1-dimethyl-ethyl)naphtho[ 2'",3'"-q]porphyrazine; zinc (II) 2,3-bis-(3-pyridyloxy) benzo[b]-10,19,28-tri( 1.1-dimethyl-ethyl)trinaphtho[2',3'-g:2",3"1:2'",3'"-q]porphyrazine; zinc (II) 2,3,18,19-tetrakis-(3-pyridyloxy) dibenzo[b,1]-10,26-di(1,1-dimethyl-ethyl)trinaphtho[ 2',3'-g:2'",3'"-q]porphyrazine; zinc (II) 2,3,9,10-tetrakis-(3-pyridyloxy) dibenzo[b,g]-17,26-di(1,1-dimethyl-ethyl)dinaphtho[2",3"-1:2'",3'"-q]porphyrazine; zinc (II) 2,3,9,10,16,17-hexakis-(3-pyridyloxy)tribenzo[b,g,1]-24-(1,1-dimethyl-ethyl)naphtho[ 2'",3'"-q]porphyrazine; zinc (II) 2-(3-N-methyl)pyridyloxy)benzo[b]-10,19,28-tri(1,1-dimethyl-ethyl)trinaphtho[2',3'-g:2",3"1:2'",3'"-q]porphyrazine monoiodide; zinc (II) 2,18-bis-(3-(N-methyl)pyridyloxy) dibenzo[b,1]-10,26-di(1,1-dimethylethyl)dinaphtho[ 2',3'-g:2'",3'"-q]porphyrazine diiodide; zinc (II) 2,9-bis-(3-(N-methyl)pyridyloxy)dibenzo[ b,g]-17,26-di(1,1-dimethylethyl) dinaphtho[2",3"-1:2'",3'"-q] porphyrazine diiodide; zinc (II) 2,9,16-tris-(3-(N-methyl-pyridyloxy)tribenzo[b,g,1]-24-( 1,1-dimethylethyl)naphtho[2'",3'"-q]porphyrazine triiodide; zinc (II) 2,3-bis-( 3-(N-methyl)pyridyloxy)benzo[ b]-10,19,28-tri(1,1-dimethylethyl)trinaphtho[2',3'-g:2",3"-1:2'",3'"-q] porphyrazine diiodide; zinc (II) 2,3,18,19-tetrakis-(3-(N-methyl)pyridyloxy)dibenzo[ b,1]-10,26-di(1,1-dimethyl)dinaphtho[2',3'-g:2''',3'''-q] porphyrazine tetraiodide; zinc (II) 2,3,9,10-tetrakis-(3-(N-methyl)pyridyloxy)dibenzo[g,g]-17,26-di(1,1-dimethylethyl)dinaphtho[2'',3''-1:2''',3'''-q] porphyrazine tetraiodide; zinc (II) 2,3,9,10,16,17-hexakis-(3-(N-methyl)pyridyloxy)tribenzo[b,g,1]-24-(1,1-dimethylethyl)naphtho[2''',3'''-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; GaPcS$_1$tBu$_3$; GaPcS$_2$tBu$_2$; GaPcS$_3$tBu$_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium(II); ruthenium(II) dipotassium[bis(triphenyl-phosphine-monosulphonate) phthalocyanine; silicon phthalocyanine bis(tri-n-hexyl-siloxy)-; silicon phthalocyanine bis(tri-phenyl-siloxy)-; HOSiPcOSi(CH$_3$)$_2$(CH$_2$)$_3$N(CH$_3$)$_2$; HOSiPcOSi(CH$_3$)$_2$(CH$_2$)$_3$N(CH$_2$CH$_3$)$_2$; SiPc[OSi(CH$_3$)$_2$(CH$_2$)$_3$N(CH$_3$)$_2$]$_2$;SiPc[OSi(CH$_3$)$_2$(CH$_2$)$_3$N(CH$_2$CH$_3$)(CH$_2$)$_2$N(CH$_3$)$_2$]$_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (U) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecyl-siloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol]hypocrellin B; 3,10-bis[4-(2-aminoethyl)morpholine]hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[ 1,12-CBr=CMeCBr(COMe)]hypocrellin B; 5,8-dibromo[1,12-CHBrC(=CH$_2$)CBr(COMe)]hypocrellin B; 5,8-dibromo[1-CH$_2$COMe, 12-COCOCH$_2$Br-]hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH(COCH$_2$I$_2$)-]hypocrellin B; 5,8-diiodo[1,12-CH$_2$C(CH$_2$I)=C(COMe)-]hypocrellin B; 2-(N,N-diethylamino) ethylaminated hypocrellin B; 3,10-bis[2-(N,N-diethylamino)-ethylamine]hypocrellin B; 4,9-bis[2-(N,N-diethyl-amino)-ethylamnine] iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo [1,12-CH$_2$C(CH$_2$I)=C(COMe)-]hypocrellin B; 8-iodo[ 1,12-CH$_2$C(CH$_2$I)=C(COMe)-]hypocrellin B; 9-methylamino iso-hypocrellin B; 3,10-bis[2-(N,N-methylamino) propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8, 15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacteriomeso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1, 6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23, 24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-(2$^3$-carboxy-2$^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis( 2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12, 17-tetrakis(2-methoxyethyl)-9-(N-t-butoxycarbonylglycinoxy) porphycene; 2,7,12,17-tetrakis (2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis( 2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(NN-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl- 3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis( 2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 $\mu$M); hematoporphyrin (400 $\mu$M); hematoporphyrin (3 $\mu$M); hematoporphyrin (18 $\mu$M); hematoporphyrin (30 $\mu$M); hematoporphyrin (67 $\mu$M); hematoporphyrin (150 $\mu$M); hematoporphyrin IX; hematoporphyrin monomer; hematoporphyrin dimer; hematoporphyrin derivative; hematoporphyrin derivative (6 $\mu$M); hematoporphyrin derivative (200 $\mu$M); hematoporphyrin derivative A (20 $\mu$M); hematoporphyrin IX dihydrochloride; hematoporphynrn dihydrochloride; hematoporphyrin IX dimethylester; haematoporphyrin IX dimethylester; mesoporphyrin dimethylester; mesoporphyrin IX dimethylester; monofornyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrint®; Photofin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylaminoformamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N-trimethylaminophenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl) porphine; tetra(4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl)porphyrin; meso-tetra(4-N-trimethylanilinium)-porphine; uroporphyrin; uroporphyrin I (17 $\mu$M); uroporphyrin IX; and uroporphyrin I (18 $\mu$M).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'"-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1'", 1'"-dibromoethenyl)-2,2':5',2"-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',2"-terthiophene; 5-(3'", 3'''-dimethylacryloyloxymethyl)-2,2':5',2''-terthiophene; 5,5''-di-(t-butyl)-2,2':5',2''-terthiophene; 5,5''-dithiomethyl-2,2':5',2''-terthiophene; 3'-ethoxy-2,2':5',2''-terthiophene; ethyl 2,2':5',2''-terthiophene-5-carboxylic acid; 5-formyl-2,2':5',2''-terthiophene; 5-hydroxyethyl-2,2':5',2''-terthiophene; 5-hydroxymethyl-2,2':5',2''-terthiophene; 5-iodo-2,2':5',2''-terthiophene; 5-methoxy-2,2':5',2''-terthiophene; 3'-methoxy-2,2':5',2''-terthiophene; 5-methyl-2,2':5',2''-terthiophene; 5-( 3'''-methyl-2'''-butenyl)-2,2':5',2''-terthiophene; methyl 2,2':5',2''-terthiophene-5-[3'''-acrylate]; methyl 2,2':5',2''-terthiophene-5-(3'''-propionate); N-allyl-2,2':5',2''-terthiophene-5-sulphonamnide; N-benzyl-2,2':5',2''-terthiophene-5-sulphonamide; N-butyl-2,2':5',2''-terthiophene-5-sulphonamide; N,N-diethyl-2,2':5',2''-terthiophene-5-sulphonamide; 3,3',4',3''-tetramethyl-2,2':5',2''-terthiophene; 5-t-butyl-5''-trimethylsilyl-2,2':5',2''-terthiophene; 3'-thiomethyl-2,2':5',2''-terthiophene; 5-thiomethyl-2,2':5',2''-terthiophene; 5-trimethylsilyl-2,2':5',2''-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4''-hydroxy)-2,2'-bithiophene; 5-(pentynyl-5''-hydroxy)-2,2'-bithiophene; 5-(3'',4''-dihydroxybutynyl)-2,2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5',2'':5'',2'''-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Particularly preferred photosensitizers are the green porphyrins, such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Of course, combinations of photosensitizers may also be used. It is preferred that the absorption spectrum of the photosensitizer be in the visible range, typically between 350 nm and 1200 nm, more preferably between 400–900 nm, and even more preferably between 600–900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

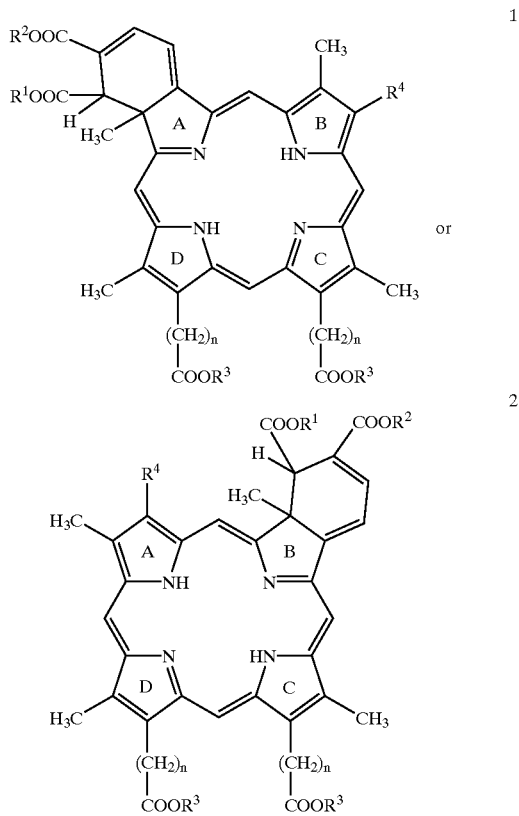

-continued

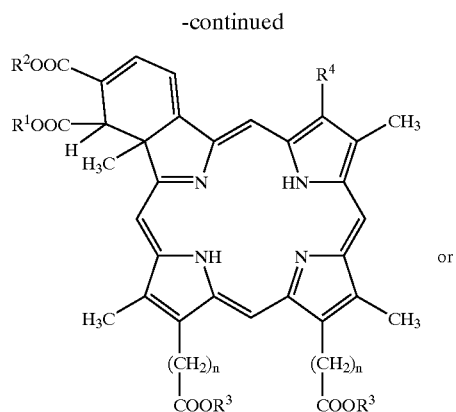
3 or

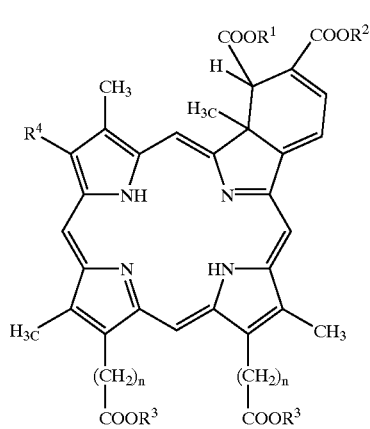
4 where $R^4$ is vinyl or 1-hydroxyethyl and $R^1$, $R^2$, and $R^3$ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin, as well as illustrations of A and B ring forms of EA6 and B3, are as follows:

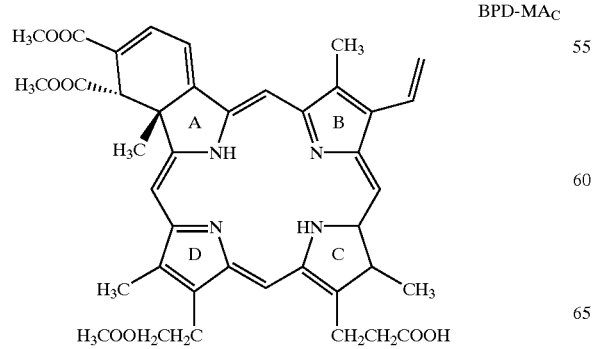
BPD-MA$_C$

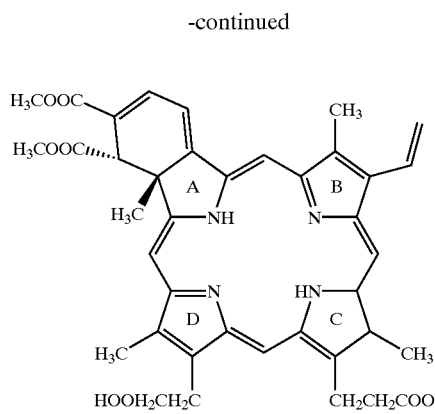
BPD-MA$_D$

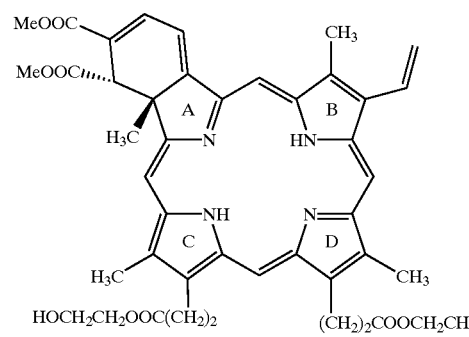
A-EA6

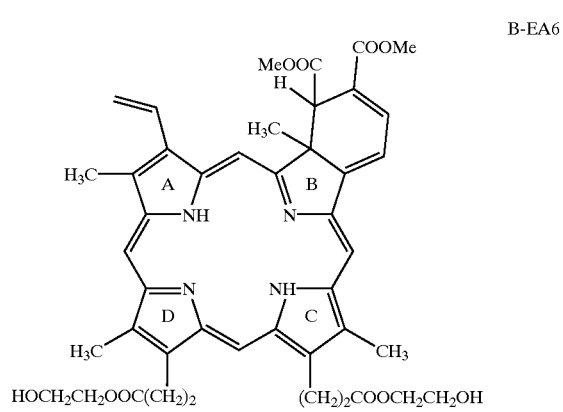
B-EA6

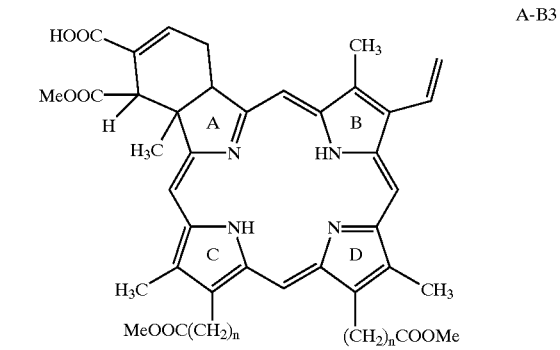
A-B3

-continued

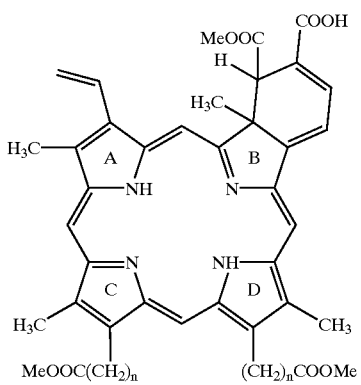

B-B3

Related compounds of formulas 3 and 4 are also useful; in general, $R^4$ will be vinyl or 1-hydroxyethyl and $R^1$, $R^2$, and $R^3$ are H or alkyl or substituted alkyl.

Microaggregates

The MA of the invention results in the production of phospholipid containing micelles, liposomes, and mixtures thereof. Phospholipids suitable for use in the invention may be any naturally occurring or synthetic phospholipid, whether saturated or unsaturated. They include, but not limited to, the following: phosphatidylcholine, phosphatidylethanolamine, phosphatidylserine, phosphatidylinositol, phosphatidylglycerol, phosphatidic acid, lysophospholipids, egg or soybean phospholipid or combinations thereof The phospholipids may be in any form, including salted or desalted, hydrogenated or partially hydrogenated, or natural, semisynthetic (modified) or synthetic. In preferred embodiments of the invention, the phospholipids used are those capable of forming liposomes, but also able to result in the production of micelles if a high energy processing step is used for size reduction of multilammelar liposomes.

Even more preferred are unsaturated phosphatidylglycerols or phosphatidylcholines with charged head groups. Such preferred embodiments include the use of negatively charged mono- or polyunsaturated phosphatidylglycerols and phosphatidylcholines such as egg phosphatidylglycerol (EPG), palmitoyloleoylphosphatidylglycerol (POPG), dioleoylphosphatidylglycerol (DOPG), dipalmitoylphosphatidylcholine (DPPC), or combinations thereof. The unsaturated fatty acid chain is preferably on the same phospholipid molecule as the charged headgroup, but alternatively, the desired combination of unsaturation and charge could be attained by using a charged saturated molecule such as DMPG together with an unsaturated phospholipid molecule. It will generally be preferable to limit the amount of the unsaturated phospholipid (in other words, not to make the whole composition from unsaturated phospholipids) because of the greater stability of saturated phospholipids. Preferably, the ratio of unsaturated charged phospholipid to the saturated phospholipid is at least about 1:99, and more preferably the ratio is at least about 3:97, and even more preferably in the range of about 10:90 or more. Most preferably, the ratio is in the range of about 40:60 to about 50:50, but may exceed 50:50.

The number of unsaturations (double bonds) in the fatty acid chain can range from about 1–6, but is more preferably about 1 to 3, and most preferably about 1 or about 2.

Without being bound by theory, and with respect to the preferential use of unsaturated lipids in the MA of the invention, it is believed that saturated acyl chains may not be sufficiently flexible during lyophilization of (removing water from) the MA. Thus in the case of liposomes, where water is removed from the core entrapped volume (for which an analogy of making raisins from grapes is applicable), unsaturated acyl chains permit more curvature in the lipid membrane and may introduce the necessary flexibility to allow shrinkage during drying. As such, the micelle containing MA of the invention are less susceptible to these effects since they likely lack an inner water core (or alternatively have a significantly smaller one). This may explain the robustness of micelle containing MA during lyophilization. The flexibility of unsaturated lipids may be a likely cause of small stable micelle structure formation during microfluidization. The presence of unsaturated lipids also lowers the phase transition temperature (liquid to gel transition) of the formulation to below room temperature, and induces a less pronounced transition. The amount of unsaturated lipid determines the degree to which the phase transition temperature is decreased. It is also believed that the presence of a charged head group on a phospholipid (for example, on phosphotidylglycerol) stabilizes small liposomes and micelles because the repulsive charge prevents fusion into larger liposomal structures.

All MA of the invention may comprise, consist of or consist essentially of any one or more phospholipids in combination with a hydrophobic agent. Preferably, the phospholipids used in the MA of the invention are either synthetic or derived from non-animal sources. More preferably, the phospholipids used in the MA of the invention include DOPG (1,2 dioleoylphosphatidylglycerol), which is a doubly unsaturated lipid of plant origin.

Phosphatidyl glycerols (PGs) may also be present in the MA of the invention. Examples of such PGs include dimyristoyl phosphatidyl glycerol (DMPG), DLPG and the like. The incorporation of such PGs may be used to contribute to the stabilization of micelles. Other types of suitable lipids that may be included are phosphatidyl ethanolamines (PEs), phosphatidic acids (PAs), phosphatidyl serines, and phosphatidyl inositols.

A range of total lipid to hydrophobic agent ratios may be use in the practice of the invention. The ratio depends on the hydrophobic agent being used, but will assure the presence of a sufficient number of lipid molecules to form stable MA. Appropriate total lipid:hydrophobic agent ratios may be from about 7:1 and higher, although lower ratios also do not exhibit adverse effects. A preferred range is from about 7:1 to 10:1. Of course all intermediate ratios within this range, such as about 8:1 and about 9:1, are within the scope of the invention. Additionally within the scope of the invention are the sub-intermediate ratios within the range, such as from about 7.1:1 to 7.9:1, about 8.1:1 to 8.9:1, and about 9.1:1 to 9.9:1, are within the scope of the invention. When the number of lipid molecules is not sufficient to form a stable complex, the lipophilic phase of the MA may become saturated with hydrophobic agent molecules. Then, any slight change in the process conditions can force some of the previously encapsulated hydrophobic agent to leak out onto the surface of the MA, or even out into the aqueous phase.

If the concentration of hydrophobic agent is high enough, it can actually precipitate out from the aqueous layer and promote aggregation of the MA. The more unencapsulated hydrophobic agent present, the higher the degree of aggregation. The more aggregation, the larger the mean aggregate size will be, and the MA will no longer be of a sufficiently small size for efficient use in steps such as filter sterilization. Thus slight increases in the lipid content can increase significantly the filterability of the liposome composition by increasing the ability to form and maintain small aggregates. This is particularly advantageous when working with significant volumes of 500 ml, a liter, five liters, 40 liters, or more, as opposed to smaller batches of about 100–500 ml or less.

When larger volumes of MA are being made, a higher molar ratio of phospholipid provides more assurance of reliable aseptic filterability by providing smaller aggregates. Moreover, the substantial potency losses that are common in scale-up batches, due at least in part to filterability problems, can thus be avoided. Another means of increasing filterability is by preparation of micelle containing MA since micelles are smaller than liposomes in general. Such micelle containing MA are more readily filter sterilized with a 0.22 micron filter and a preferred embodiment of the invention. Additional advantages in MA containing the smaller micelles is reduced loss of the active hydrophobic agent via large aggregates lost during filtering or other processes; and the stability of smaller aggregates after reconstitution. Thus a preferred embodiment of the invention is where the hydrophobic agent is present in amounts, or in ratios, that favor micelle formation.

When a combination of phospholipids is used in the MA of the invention, a range of relative lipid ratios may be used in combination with the total lipid:hydrophobic agent ratios described above. Appropriate lipid ratios for combinations of two phospholipids range from about 50:50 to about 97:1. Of course all intermediate ratios within this range, such as about 70:30, about 80:20 and about 90:10, are within the scope of the invention. As indicated by the use of the 99:1 ratio, sub-intermediate ratios within the range, such as from about 71:29 to 79:21, about 81:19 to 89:11, and about 91:9 to 97:3, are within the scope of the invention. Examples of combinations of two phospholipids where such ratios may be used include DMPC:DMPG, DMPC:EPG, DMPC:POPG and DMPC:DOPG. An additional example is DMPC: EPG, preferably at a ratio of about 5:3 respectively. With this combination, even higher hydrophobic agent:lipid ratios, such as 1:10, 1:15, or 1:20, respectively, may be used.

A particularly preferred embodiment of the MA of the invention comprises hydrophobic agents in an 8:1 total phospholipid:hydrophobic agent ratio with a 60:40 lipid ratio of a DMPC:DOPC combination containing antioxidants BHT and AP. In particular, hydrophobic agents such as EA6 and/or BPD-MA may be used in such MA. Also preferred are MA compositions comprising EA6 in small liposomes comprising lipids and other components as described herein.

Antioxidants

In preferred embodiments comprising the use of unsaturated phospholipids, the invention encompasses the use of antioxidants to prevent oxidation of the phospholipids. Auto-oxidation of unsaturated acyl chains has been known to be a problem for long-term storage of liposome formulations. Failure to prevent oxidative breakdown of unsaturated phospholipids results in subcomponents such as lyso lipids and fatty acids, which may be undesirable in some MA compositions. As such, antioxidants suitable for inclusion in phospholipid containing microaggregates to improve long-term storage are known in the art. Examples of such antioxidants include butylated hydroxytoluene (BHT), alpha-tocopherol, and ascorbyl palmitate (AP) as well as pH buffering agents such as phosphates and glycine. Preferably, BHT is present at about 0.01–0.02% by weight and AP at about 0.1–0.2% by weight.

BHT is hydrophobic and would be expected to remain in the lipophilic environments of the MA of the invention. BHT has the ability to prevent chain propagation during auto-oxidation by accepting radicals formed during the oxidative breakdown of lipids. Ascorbic acid has the capacity to act as an antioxidant and to act with other antioxidants such as alpha-tocopherol. It has been shown that the BHT/ascorbic acid system allows for BHT regeneration, following its conversion to a phenoxyl radical after free radical scavenging from oxidized lipids, thereby resulting in the appearance of ascorbyl radicals. This latter factor justifies the relative weight ration of AP to BHT described above. AP was used in place of ascorbic acid because the hydrophobic nature of the former would be expected to concentrate the antioxidant within lipophilic environments.

Another anti-oxidation considerations is the filling of container headspaces with nitrogen gas and the sealing of such containers. Additionally, and because metal ions can catalyze oxidative processes, the use of high quality drug, excipients, and containers, the judicious cleaning of manufacturing equipment, and the appropriate use of metal ion chelators are preferred.

Cryoprotective Agents and Isotonic Agents

In a preferred embodiment of the invention, the MA are stabilized by lyophilization. An advantage to the micelle containing MA of the invention is the fact that micelles may be more readily lyophilized in comparison to liposomes due to the absence of a water core. Lyophilization of liposomes require the passage of water across at least one lipid bilayer, resulting in increased processing times and expense. The absence of a water core also permits micelles to have a greater concentration of phospholipid per unit volume. Thus a larger amount of hydrophobic agent can be solubilized by the phospholipid per unit volume of micelle. This permits the final micelle MA delivery vehicle to have a higher drug density per unit volume than other delivery vehicles, such as liposomes alone.

MA of the invention may contain a cryoprotectant for stabilizing the MA during lyophilization. Alternatively, the physical structures of the MA can be preserved by the presence of sufficient water after lyophilization. This is may be accomplished by appropriate control of the degree of lyophilization. Since there is no entrapped volume in micelles, the micelle containing MA of the invention facilitates greater control over water soluble components, like solvent or salt, to be removed in the preparation of delivery vehicles requiring such removal.

Any cryoprotective agent known to be useful in the art of preparing freeze-dried formulations, such as di- or polysaccharides or other bulking agents such as lysine, may be used in the claimed invention. Further, isotonic agents typically added to maintain isomolarity with body fluids may be used. In preferred embodiments, a di-saccharide or polysaccharide is used and functions both as a cryoprotective agent and as an isotonic agent. In an especially preferred embodiment, the disaccharide or polysaccharide is selected from among the group consisting of lactose, trehalose, maltose, maltotriose, palatinose, lactulose or sucrose, with lactose or trehalose being preferred. Effective sugars such as trehalose and lactose are capable of hydrogen bonding to the phospholipidhead group in place of water. It has also been hypothesized that effective sugars also act a as a spacing matrix to decrease the opposition of phospholipids on the exterior of adjacent MA such as liposomes.

When the process of hydrating a lipid film is prolonged, larger liposomes tend to be formed, and hydrophobic agents may even precipitate. The addition of a disaccharide or polysaccharide provides the largest surface area for depositing a thin film of MA and virtually instantaneous subsequent hydration. This thin film provides for faster hydration so that, when the MA are initially formed by adding the aqueous phase (hydrated), the MA are of a smaller and more uniform particle size. This provides significant advantages in terms of manufacturing ease.

However, it is also possible that, when a saccharide is present in the composition of the invention, it is added after dry lipid film formation, as a part of the aqueous solution used in hydration. In a particularly preferred embodiment, a saccharide is added to the dry lipid film of the invention during hydration.

Disaccharides or polysaccharides are preferred to monosaccharides for this purpose. To keep the osmotic pressure of the MA compositions of the invention similar to that of blood, no more than 4–5% monosaccharides should be added. In contrast, about 9–10% of a disaccharide can be used without generating an unacceptable osmotic pressure. The higher amount of disaccharide provides for a larger surface area, which results in smaller particle sizes being formed during hydration of the lipid film.

Also, when present, the disaccharide or polysaccharide is formulated in a preferred ratio of about 10–20 saccharide to 0.5–6.0 total phospholipids, respectively, even more preferably at a ratio from about 10 to 1.5–4.0. In one embodiment, a preferred but not limiting formulation is lactose or trehalose and total phospholipids in a ratio of about 10 to 0.94–1.88 to about 0.65–1.30, respectively.

The presence of the disaccharide or polysaccharide in the composition not only tends to yield MA having extremely small and narrow aggregate size ranges, but also provides MA compositions in which the hydrophobic agents, such as a hydro-monobenzoporphyrin photosensitizer, may be stably incorporated in an efficient manner, i.e., with an encapsulation efficiency approaching 80–100%. Moreover, MA made with a saccharide typically exhibit improved physical and chemical stability, such that they can retain an incorporated hydrophobic agent, such as hydro-monobenzoporphyrin photosensitizer, without leakage upon prolonged storage, either as a reconstituted aqueous suspension or as a cryodesiccated powder.

Freeze-Drying

Once formulated, the MA of the invention may be freeze-dried for long-term storage if desired. For example, BPD-MA, a preferred hydro-monobenzoporphyrin photosensitizer, has maintained its potency in a cryodesiccated MA composition for a period of at least nine months at room temperature, and a shelf life of at least two years has been projected. If the composition is freeze-dried, it may be packed in vials for subsequent reconstitution with a suitable aqueous solution, such as sterile water or sterile water containing a saccharide and/or other suitable excipients, just prior to use. For example, reconstitution may be by simply adding water for injection just prior to administration.

Various lyophilization techniques are known in the art. For example, MA containing vials of the invention may be first frozen to −45° C. and then held there for a period of up to about 90 minutes. This may be followed by a high vacuum primary drying cycle wherein the temperature is increased slowly to up to about 10° C. for a period usually on the order of about 50 hours. This may be followed by a 20° C. secondary drying cycle of up to about 24 hours. Once the lyophilizer pressure stabilizes at about 55–65 mTorr (73–87 microbar), the cycle is terminated. Thereafter, the vials may be sealed after overlaying with nitrogen gas. A general rule for freeze-drying is that a solid, brittle, non-collapsed, and homogenous cake is preferred for successful re-hydration.

Additionally, the use of lyophilization may prevent hydrolysis of hydrophobic agents susceptible to such reactions. For example, the photosensitizer BPD-MA may be hydrolyzed to BPD-DA.

Size

In one aspect of the invention, the MA are of a sufficiently small and narrow size that the aseptic filtration of the composition through a 0.22 micron hydrophilic filter can be accomplished efficiently and with large volumes of 500 ml to a liter or more without significant clogging of the filter. As such micelle and small liposome containing MA are a preferred embodiment of the invention. Moreover, and given their smaller size, the MA of the invention may mainly, or predominantly, contain hydrophobic agent bearing micelles. The MA of the invention may contain greater than about 50%, greater than about 60%, greater than about 75%, greater than about 80%, greater than about 90%, and greater than about 95% micelles. Even more preferably, the MA of the invention may contain greater than about 97%, about 98%, or about 99% micelles. Most preferably in desired circumstances, the MA of the invention consist only of micelles. Alternatively, the MA of the invention may in some circumstances (when an extrusion process is used for size reduction of multilammelar liposomes, rather than a high energy process such as microfluidization) contain up to 100% liposomes.

Micelles refer to microaggregates with the hydrophobic (lipophilic) "tail" portion of the phospholipids generally oriented toward the interior of the micelle. Preferably, micelles have the "tail" portion generally oriented toward the center of the micelle. Micelles do not have a bilayer structure and so are not considered vesicles or liposomes. The micelles of the invention have average diameters of less than about 30 nm (nanometers). Preferably, they have average diameters of less than about 20 nm.

Liposomes refer to microaggregates comprising at least one phospholipid bilayer, composed of two lipid monolayers having a hydrophobic "tail" region and a hydrophilic "head" region. The structure of the membrane bilayer is such that the hydrophobic (nonpolar) "tails" of the lipid monolayers orient themselves towards the center of the bilayer, while the hydrophilic "heads" orient themselves toward the aqueous phase. They generally comprise completely closed, lipid bilayer membranes that contain an entrapped aqueous volume. Given the bilayer structure, a significant portion (up to about half) of the phospholipids will have their hydrophobic (lipophilic) portion generally oriented away from the center of the liposome. Liposomes include unilamellar vesicles having a single membrane bilayer or multilamellar vesicles having multiple membrane bilayers, each bilayer being separated from the next by an aqueous layer. The average diameters of liposomes are larger than that of micelles.

In liposomes, a hydrophobic agent can be entrapped in the aqueous phase of the liposome or be associated with the "tail" portion of phospholipids in the lipid bilayer. In micelles, a hydrophobic agent is left to associate only with the "tail" portion of phospholipids in the core of the micelle. Additionally, both micelles and liposomes may be used to help "target" a hydrophobic drug to an active site or to solubilize hydrophobic drugs for parenteral administration.

One aspect of the present invention uses this ability to form micelles and liposomes by the same mixture of hydrophobic agent and phospholipids. This would result in MA that have a bimodal distribution in their diameters, indicating the presence of both micelles and liposomes. In another aspect of the invention, the micelles and liposomes are form under conditions that favor one type of microaggregate over the other in the same mixture. Conditions that favor micelle formation include the presence of low salt in the mixture as well as the use of low salt aqueous solution for hydrating the dried mixture. "Low salt" refers to conditions containing less than about 0.1 N free cations or anions. Preferably, it refers to less than about 0.01 N free ions. More preferably it refers to less than about 0.001 N free ions.

Preferred MA of the invention have an average aggregate size diameter of well below about 300 nm, more preferably below from about 200 nm. Most preferably, the MA of the invention have an average aggregate size diameter below about 100 nm, and sometimes, depending on the conditions chosen, in the range of 10–50 nm. The size of the microaggregates made comprising QLT 0074, DOPG and DMPC (see Example 1 below) have been sized using three different methods (using a NICOMP 370 Submicron Particle Sizer, by freeze fracture analysis and by size exclusion HPLC). Freeze fracture analysis showed a mixture of micelles (7–15 nm in diameter), and relatively few liposomes (between 6- and 270 nm diameter). Size exclusion HPLC indicated mean particle size of 28 nm when tested in four different media (PBS, 0.9% sodium chloride, 9.2% lactose and 5% dextrose) with a range or 25–35 nm.

As discussed herein, the invention controls four major parameters that can affect the ease of aggregate size reduction to an unexpected degree. As a result, the filterability, particularly with standard aseptic filtration, is significantly improved in the MA of the invention. These parameters are (1) the production of micelles and small liposomes by use of low salt conditions; (2) suitable molar ratio of hydro-monobenzoporphyrin photosensitizer to total phospholipids; (3) temperature during the hydration step; and (4) temperature during the homogenization or size reduction step. The latter two parameters are discussed below.

Filterability can be tested by passing a MA composition through a Microfluidizer™ three times and withdrawing a sample with a syringe. The syringe is connected to a 0.22 micron hydrophilic filter and then placed in a syringe pump. The constant rate of piston movement is set at 10 ml/min, and filtrate is collected until the filter becomes blocked by large aggregates. The volume of the filtrate is then measured and recorded in terms of ml/cm$^2$ or g/cm$^2$, with a square centimeter being the effective filtration area. Thus, filterability for the purposes of the invention is defined as the maximum volume or weight of MA composition that can be filtered through a 0.22 micron filter.

The MA of the invention may be used as a delivery vehicle for the constituent hydrophobic agent to target any cell or tissue for which contact with the agent is desired. In preferred embodiments of the invention, the agent is a photosensitizer to be delivered prior to light irradiation as part of photodynamic therapy (PDT). Particularly preferred MA of the invention comprise a hydro-monobenzoporphyrin photosensitizer, including BPD-MA and EA6, for use in photodynamic therapy (PDT) or diagnosis.

The MA of the invention also preferably comprises micelles which are readily, and significantly, destabilized in the presence of proteins, salts, charged elements, and/or polymers. Such MA are well suited as a pharmaceutical formulation to deliver hydrophobic drugs to fluids such as blood, which contains proteins, salts, charged elements and polymers. Given the ability to destabilize after delivery to target conditions, the MA of the invention can rapidly deliver hydrophobic agents to targets such as the bloodstream, where the drugs may be picked up or transferred to blood components for farther transport and/or targeting based on the components' specificities. As such, the MA can be considered "fast breaking" in that the MA is stable in vitro but, when administered in vivo, the hydrophobic drug (such as a photosensitizer) is rapidly released into the bloodstream where it associates with blood components such as serum lipoproteins. Another beneficial effect of this transfer is reduced depositing of hydrophobic agents in various organs, especially the liver. As such, the pharmokinetics of delivering the hydrophobic agent with such micelles are altered compared to the use of other delivery vehicles or systems, such as those that do not release the agent rapidly or those that do not transfer the agent to blood components.

Preparation

Methods for the production of the MA of the invention comprise, consist of, and/or consisting essentially of the combination of hydrophobic agents and phospholipids and subjecting them to conditions capable of forming micelles, small liposomes or combinations thereof. Preferably, the methods comprise the use of phospholipids capable of forming lipid bilayers and result in the production of stable micelles and/or small liposomes. The resultant MA, especially those comprising or consisting of micelles of the invention, do not contain detergents normally used for micelle production. The absence of detergents can markedly reduce toxicity known to result in hemolysis and kidney damage. To favor micelle formation, the MA of the invention are formulated under low salt conditions because, as noted above, the micelles of the invention are destabilized by salt.

Generally, the MA of the invention are produced by dissolving the desired MA constituent component molecules (such as desired phospholipids, hydrophobic agent, and optionally antioxidants and cryoprotectants) into a solvent to form an "intermediate complex". Preferred solvents are organic or otherwise non-aqueous. Suitable organic solvents include any volatile organic solvent, such as diethyl ether, acetone, methylene chloride, chloroform, piperidine, piperidine-water mixtures, methanol, tert-butanol, dimethyl sulfoxide, N-methyl-2-pyrrolidone, and mixtures thereof. Preferably, the organic solvent is water-immiscible, such as methylene chloride, but water immiscibility is not required. In any event, the solvent chosen should not only be able to dissolve all of the components of the lipid film, but should also not react with, or otherwise deleteriously affect, these components to any significant degree.

The organic solvent is then removed from the resulting solution to form a dry lipid film by any known laboratory technique that is not significantly deleterious to the dry lipid film and the hydrophobic agent. Such techniques include any that remove the solvent via its gaseous phase, including evaporation or vacuum. In one embodiment, the solvent is removed by placing the solution under a vacuum until the organic solvent is evaporated. The solid residue is the dry lipid film of the invention, which contains aggregates of the MA components, considered the "presome". The thickness of the lipid film is not critical, but usually varies from about 30 to about 45 mg/cm$^2$, depending upon the amount of solid residual and the surface area of the vessel which contains it. In another embodiment of the invention, the solvent is removed as part the "presome" process of Nanba et al. (U.S. Pat. No.5,096,629, which is hereby incorporated by reference as if fully set forth), which heats the "intermediate complex" and subjects it to dryness via an instantaneous vacuum drying system such as the CRUX 8B™ (Orient Chemical Ind., Ltd., Japan) to produce a lipid powder containing aggregates of the MA components.

Once formed, the film or powder may be stored for an extended period of time, preferably not more than 4 to 21 days, prior to hydration. Storage may be under an appropriate gas, such as argon. While the temperature during a lipid film or powder storage period is also not an important factor, it is preferably below room temperature, most preferably in the range from about −20 to about 4° C. One advantage to the Nanba et al. "presome" process is the reduction of batch to batch variability seen with thin film, which arises due to the use of multiple batches in evaporation vessels.

The dry lipid film or powder may be hydrated with an aqueous solution, preferably containing a disaccharide or polysaccharide if not previously present. This will result in the formation of large multilammelar liposomes that can be further processed by extrusion or a high energy process, such as microfluidization to form the desired particle size. Examples of useful aqueous solutions used during the hydration step include sterile water, or a dilute solution of lactose. In one embodiment of the invention, the solution is physiologically isotonic, such as 9.2% lactose, which permits bolus injections. Preferably the aqueous solution is sterile. Most preferably for the production of micelles and the stabilization of small liposomes, the solution is low salt. It is believed that the presence of salts neutralizes the negative repulsive charges that prevent the aggregation or fusion of these small particles into larger liposomes.

The volume of aqueous solution used during hydration can vary greatly, but should not be so great as about 98% nor so small as about 30–40%. A typical range of useful volumes would be from about 50 or 60% to about 95%, preferably about 75% to about 95%, more preferably about 80% to about 90%, and most preferably about 85% to 90%. Of course all subranges from about 30% to about 98% are included as part of the invention.

The physical manipulation of material during hydration may be conducted by a variety of means, including mixing and rotating on a rotary evaporator, manual swirling of vessels, and the use of standard laboratory stirrer or shaker means (including stir bars with stir plates, high shear mixers, paddles and combinations thereof). Preferred in the practice of the invention are high agitation methods, such as the use of high-shear mixing or egg-shaped stir bars.

Upon hydration, coarse aggregates are formed that incorporate a therapeutically effective amount of the hydrophobic agent. The "therapeutically effective amount" can vary widely, depending on the tissue to be treated and whether the hydrophobic agent is coupled to a target-specific ligand, such as an antibody or an immunologically active fragment. Typically, the therapeutically effective amount is such to produce a dose of hydrophobic agent within a range of from about 0.1 to about 20 mg/kg, preferably from about 0.15–2.0 mg/kg and, even more preferably, from about 0.25 to about 0.75 mg/kg. Preferably, the w/v concentration of the hydrophobic agent in the "intermediate complex" ranges from about 0.1 to about 8.0–10.0 g/L, when the mixture becomes such a thick gel that it is not possible to handle or administer to a subject by the usual means. Most preferably, the concentration is about 2.0 to 2.5 g/L.

It should be noted that if the agent is a photosensitizer, the various parameters used for selective photodynamic therapy are interrelated. Therefore, the therapeutically effective amount should also be adjusted with respect to other parameters, for example, fluence, irradiance, duration of the light used in photodynamic therapy, and the time interval between administration of the photosensitizing agent and the therapeutic irradiation. Generally, all of these parameters are adjusted to produce significant damage to tissue deemed undesirable, such as neovascular or tumor tissue, without significant damage to the surrounding tissue, or to enable the observation of such undesirable tissue without significant damage to the surrounding tissue.

The hydration step should take place at a temperature that does not exceed the glass transition temperature of the phospholipid and hydrophobic agent aggregates formed. For photosensitizers of the invention, this temperature is about 30° C. Preferably the temperature is at room temperature or lower, such as from 10–25, or even more preferred from 15–20° C. or 17–22° C. An especially preferred temperature is about 21° C. The glass transition temperature of the phospholipid and hydrophobic agent aggregates can be measured by using a differential scanning microcalorimeter. Madden et al. ("Spontaneous vesiculation of large multilamellar vesicles composed of saturated phosphatidylcholine and phosphatidylglycerol mixtures." Biochemistry, Vol. 27, pp. 8724–8730, (1988)) describe the effects of temperature and ionic strength on vesicle formation.

The use of unsaturated charged lipids as encompassed by the invention may effectively lower the phase transition temperature Tc (liquid to gel transition) of the formulation to below room temperature and induce a less pronounced transition. The amount of unsaturated lipid determines the degree of Tc lowering.

The particle sizes of the coarse aggregates first formed during hydration are then homogenized to a more uniform size and/or reduced to a smaller size range of about less than about 50 to about 300 nm, depending on the method of size reduction used. Preferably, this homogenization and/or reduction is also conducted at a temperature below the glass transition temperature of the hydrophobic agent-phospholipid complex formed in the hydration step. For photosensitizers of the invention, such temperature does not exceed about 30° C., and is preferably below room temperature of about 25° C. It has been found that the homogenization temperature with photosensitizers is preferably at room temperature or lower, e.g., 15–20° C. At higher homogenization temperatures, such as about 32–42° C., the relative filterability of the MA composition may improve initially due to increased fluidity as expected, but then, unexpectedly, tends to decrease with continuing agitation due to increasing particle size.

Various high-speed agitation or high energy system manipulation processes may be used during the homogenization step. Examples of such processes include microfluidization (liquid jet milling), high shear mixing, and sonication. While effective, sonication is not ideal for use in large scale production of MA. Processing through the aforementioned high energy system results in the production of small particles, usually a mixture of small liposomes and micelles. Extrusion, is another method of size reduction. Extrusion results in the production of small liposomes (as small as 50 to 100 nm), but micelles have not been observed by the inventors in production by this procedure. Extrusion involves the forcing of hydrated material, under pressure and at temperatures known to make liposome formulations fluid, through membrane filters of defined pore sizes. While adequate for laboratory scale batches of material, extrusion may not be ideal for large scale processes since 1) the pores become clogged even at high pressures of greater than 1000 psi, 2) the surface area of the filter membrane and extruder volume are limitations, and 3) multiple discontinuous passes through the extruder increases the likelihood of differences between batches.

Devices for the above described processes include a Microfluidizer™ (such as a Microfluidics™ Model 110F); a sonicator; a high-shear mixer; a homogenizer; a standard laboratory shaker or stirrer, or any other agitation device. Of course modifications in such processes to suit the particular hydrophobic agent of interest and formation of the desired MA are within the scope of the invention. In one preferred embodiment of the invention, these processes are used for the production of MA containing mainly micelles.

Such processes may be used to produce MA various ratios of micelles, liposomes and combinations thereof. In embodiments where both micelles and liposomes are produced, they may be separated by the bimodal size distribution seen in combinations of the two. This arises from the significantly smaller size of micelles in comparison to liposomes. The analysis of MA size may be performed by methods including electron microscopy, to exclude large aggregates as liposomes, and use of a particle sizer, which may be used in combination with fitting routines for uni- and bimodal distributions. Another method is by use of manganese chloride ($Mn^{2+}$) mediated nuclear magnetic resonance ($^{31}$P-NMR), where $^{31}$Phosphorus labeled headgroups of lipids on the inner layer of a liposome lipid bilayer are not quenched by $Mn^{2+}$ because $Mn^{2+}$ cannot readily cross the bilayer to enter the entrapped volume. Thus liposomes will produce a residual NMR signal of about 30–40% for large and small liposomes after adding $Mn^{2+}$. All $^{31}$P-labeled headgroups of lipids of a micelle, however, are on the surface and thus fully exposed to $Mn^{2+}$ quenching. Thus micelles produce no remaining NMR signal due to quenching after adding $Mn^{2+}$ (see FIG. 1).

In a preferred embodiment, a high pressure device such as a Microfluidizer™ is used for agitation. Some models of microfluidization systems are continuous and batch size scalable processors. Microfluidization uses high pressure streams of hydrated material that collide at ultra-high velocities in precisely defined microchannels. In the interaction chamber, two streams of fluid at a high speed collide with each other at a 90° angle. The combined forces of shear, impact and cavitation result in the production of liposomes and micelles. In microfluidization, a large amount of heat is generated during the short period of time during which the fluid passes through a high pressure interaction chamber. As the microfluidization temperature increases, the fluidity of the membrane also increases, which initially makes particle size reduction easier, as expected. For example, filterability can increase by as much as four times with the initial few passes through a Microfluidizer™ device. The increase in the fluidity of the bilayer membrane promotes particle size reduction, which makes filtration of the final composition easier. In the initial several passes, this increased fluidity mechanism advantageously dominates the process.

However, as the number of passes and the temperature both increase, more of the hydrophobic agent molecules are apparently squeezed out in cases involving liposomes, increasing the tendency of the liposomes to aggregate into larger particles. At the point at which the aggregation of vesicles begins to dominate the process, the sizes cannot be reduced any further.

For this reason, in the methods of the invention, the homogenization temperature is cooled down to and maintained at a temperature no greater than room temperature after the composition passes through the zone of maximum agitation, e.g., the interaction chamber of a Microfluidizer™ device. An appropriate cooling system can easily be provided for any standard agitation device in which homogenization is to take place, e.g., a Microfluidizer™, such as by circulating cold water into an appropriate cooling jacket around the mixing chamber or other zone of maximum turbulence. While the pressure used in such high pressure devices is not critical, pressures from about 10,000 to about 16,000 psi are not uncommon.

Maintaining the hydration temperature and the homogenizing/reducing step at a temperature below 30° C. would not have been expected to produce smaller particle sizes. In fact, the invention is contrary to the conventional wisdom that small particle sizes are achieved by increasing rather than decreasing these temperatures. See, e.g., M. Lee et al., "Size Distribution of Liposomes by Flow Field-Flow Fractionation", *J. Pharm. & Biomed. Analysis,* 11:10, 911–20 (1993), equation (6) showing particle diameter "d" as inversely related to temperature "T", and FIG. 6b therein showing liposome preparation I (prepared at about 70° C.) having smaller particle sizes than preparation II (prepared at about 23° C.).

As a last step, the MA compositions of the inventions are preferably aseptically filtered through a filter having an extremely small pore size, i.e., 0.22 micron. While other sterilization methods, such as heating and X-ray irradiation are known, in the art, the use of such methods may result in irreversible structural changes in lipids and hydrophobic agents such as many photosensitizers. A wide variety of filtration systems are known in the art, including Durapore TP cartridges, Millipak 100, Millidisk 40S, and millidisk MCGL. Filter pressures used during sterile filtration can vary widely, depending on the volume of the composition, the density, the temperature, the type of filter, the filter pore size, and the size of the MA. However, as a guide, a typical set of filtration conditions would be as follows: filtration pressure of 15–25 psi; filtration load of 0.8 to 1.5 ml/cm²; and filtration temperature of about 25° C. Preferably, the hydrophilic Millidisk 40S is used at a load of approximately 1 ml/cm².

A typical general procedure for producing hydro-monobenzoporphyrin photosensitizer containing MA of the invention is described below with additional exemplary detail:

(1) Sterile filtration of methylene chloride as organic solvent through a hydrophobic, 0.22 micron filter.

(2) Addition of DMPC:EPG:BPD-MA at a ratio of 4.7:3.25:1 and excipients to the filtered organic solvent, dissolving both the excipients and the photosensitizer to form the "intermediate complex".

(3) Filtration of the resulting solution through a 0.22 micron hydrophobic filter.

(4) Transfer of the filtrate to a rotary evaporator apparatus, such as that commercially available under the name Roto-evaporator.

(5) Removal of the organic solvent to form a dry lipid film.

(6) Analysis of the lipid film to determine the level of organic solvent concentration; optionally continuing removal until the level of organic solvent is below 0.01%, (7) Preparation of a 10% lactose solution. If the MA formulation is to be injected, this solution should be injectable.

(8) Filtration of the lactose solution through a 0.22 micron hydrophilic filter.

(9) Hydration of the lipid film with the filtered 10% lactose solution to form coarse aggregates.

(10) Reduction of the particle sizes of the coarse aggregates by passing them through a Microfluidizer™, optionally at 9000 psi (pounds per square inch) for about 5 discrete passes to produce micelles.

(11) Determination of the reduced aggregated size distribution of MA.

(12) Aseptic filtration of the MA composition through a 0.22 micron hydrophilic filter. (Optionally, the solution may first be pre-filtered with a 5.0 micron or smaller pre-filter.)

(13) Analysis of photosensitizer potency.

(14) Filling of vials with the MA composition.

(15) Freeze-drying.

The above may be adapted for the selective production of micelles by conducting all appropriate steps under low salt conditions to favor subsequent micelle production after hydration. As such, salt based bulking agents must not be used. In such applications, the resulting micelles are on the order of about 15 nm in diameter, which is at the lower limit for feasible liposome sizes. The micelle structure was confirmed by use of $^{31}$P-NMR.

An alternative general procedure for producing hydro-monobenzoporphyrin photosensitizer containing MA of the invention by use of a "presome" process of Nanba et al. (see U.S. Pat. No. 5,096,629) is described below with additional exemplary detail:

(1) Sterile filtration of methylene chloride as organic solvent through a hydrophobic, 0.22 micron filter.

(2) Addition of DMPC:DOPG at a ratio of 60:40 with a total lipid:EA6 at a ratio of 8:1 and antioxidants BHT and AP to the filtered organic solvent, dissolving both the excipients and the photosensitizer to form the "intermediate complex".

(3) Filtration of the resulting solution through a 0.22 micron hydrophobic filter.

(4) Transfer of the filtrate to liquid tank followed by feeding to a tubular heater heated externally.

(5) Removal of the organic solvent by sending the heated mixture into a vacuum chamber of no more than 300 mm Hg at a speed over 0.1 times the speed of sound to instantaneously dry the mixture to form lipid powder.

(6) Analysis of the lipid powder to determine the level of organic solvent concentration; optionally continuing removal until the level of organic solvent is below 0.01%, (7) Preparation of a 10% lactose solution. If the MA formulation is to be injected, this solution should be injectable.

(8) Filtration of the lactose solution through a 0.22 micron hydrophilic filter.

(9) Hydration of the lipid powder with the filtered 10% lactose solution to form coarse aggregates.

(10) Dispersion of the coarse aggregates by stirring them at high rpm at a temperature below the glass transition temperature of the photosensitizer and phospholipid containing aggregates.

(11) Determination of the reduced aggregated size distribution of MA.

(12) Aseptic filtration of the MA composition through a 0.22 micron hydrophilic filter. (Optionally, the solution may first be pre-filtered with a 5.0 micron or smaller pre-filter.)

(13) Analysis of photosensitizer potency.

(14) Filling of vials with the MA composition.

(15) Freeze-drying.

One means of conducting the above instantaneous drying is by use of a vacuum drying system such as the CRUX 8B™ product of Orient Chemical Ind., Ltd., Japan. Moreover, the above dispersion step may be at speeds of about 10,000 rpm, or ranging from 8000 to 15,000 rpm. Such a "presome" process may also be adapted for the selective production of micelles by conducting all appropriate steps under low salt conditions to favor subsequent micelle production after hydration. As such, salt based bulking agents must not be used.

As described above, the practice of the methods of the invention for MA production may be conducted with a variety of phospholipids and processes. The invention includes the observation, beyond the use of low salt conditions, that the use of charged, unsaturated phospholipids, such as EPG and DOPG, as well as high energy processing (such as microfluidization and sonication), appears to favor the formation of micelles in otherwise liposome forming combinations of phospholipids and hydrophobic agents. The use of unsaturated phospholipids provides a number of desirable characteristics. These include the ability to conduct MA production steps at room temperature and to produce smaller MA when used in combination with saturated lipids.

Administration and Use

The use of the hydrophobic agents incorporated in the MA of the invention may be for any appropriate pharmaceutical, agricultural or industrial application. With incorporated photosensitizers, the MA may be used for any condition or in any method for which the photosensitizers are appropriate in combination with exposure to light or other electromagnetic radiation. These include, but are not limited to, the diagnosis or treatment of cancer, the reduction of activated leukocytes, the treatment of ocular disorders, the treatment and prevention of neovasculature and angiogenesis, the destruction of viruses and cells infected thereby, the treatment of atherosclerotic plaques, the treatment of restenosis, and others. In addition, many photosensitizers may be photoactivated by appropriate excitation wavelengths to fluoresce visibly. This fluorescence can then be used to localize a tumor or other target tissue. By incorporating hydrophobic agents in the MA of the invention, more efficient packaging, delivery and hence administration of the agents can be obtained.

Generally speaking, the MA of the invention may be applied in any manner identical or analogous to the administration of micelles and liposomes. The concentration of the hydrophobic agent in the MA of the invention depends upon the nature of the agent as well as the nature of the administration desired. This dependency also exists in application of hydro-monobenzoporphyrin photosensitizers via MA.

The MA compositions and formulations of the invention may be administered parenterally or by injection. Injection may be intravenous, subcutaneous, intramuscular, intrathecal, or even intraperitoneal. However, the MA may also be administered by aerosol intranasally or intrapulmonarally, or topically. Formulations designed for timed release are also with the scope of the invention.

The quantity of hydrophobic agent MA formulation to be administered depends on the choice of active agents, the conditions to be treated, the mode of administration, the individual subject, as well as the skill, experience and judgement of the practitioner. Generally speaking, however, dosages in the range of 0.05–10 mg/kg may be appropriate. The foregoing range is, of course, merely suggestive, as the number of variables in regard to an individual treatment regime is large. Therefore, considerable excursions from these recommended values are expected.

For example, and with the use of photosensitizers as a diagnostic in localizing tumor tissue or in localizing atherosclerotic plaques, the MA compositions of the invention are administered systemically in the same general manner as is known with respect to photodynamic therapy. The waiting period to allow the drugs to clear from tissues to which they do not accumulate is approximately the same, for example, from about 30 minutes to about 10 hours. After the compositions of the invention have been permitted to localize, the location of the target tissue is determined by detecting the presence of the photosensitizer.

In diagnosis, the photosensitizers incorporated into MA may be used along with, or may be labeled with, a radioisotope or other detecting means. If this is the case, the detection means depends on the nature of the label. Scintigraphic labels such as technetium or indium can be detected using ex vivo scanners. Specific fluorescent labels can also be used but, like detection based on fluorescence of the photosensitizers themselves, these labels may require prior irradiation.

For activation of the photosensitizer applied by the MA of the invention, any suitable absorption wavelength is used. This can be supplied using the various methods known to the art for mediating cytotoxicity or fluorescence emission, such as visible radiation, including incandescent or fluorescent light sources or photodiodes such as light emitting diodes. Laser light can also be used for in situ delivery of light to a localized photosensitizer. In a typical protocol, for example, several hours prior to irradiation, approximately 0.5–1.5 mg/kg of green porphyrin photosensitizer containing MA is injected intravenously and then excited by an appropriate wavelength.

The following example is presented to describe the preferred embodiments, utilities and attributes of the present invention, but they not meant to limit the invention. The invention is not to be limited to the particular photosensitizer used in the Example.

EXAMPLE 1

Production of QLT0074 for Injection

Five hundred mL methylene chloride was added to 0.001 g butylated hydroxytoluene, 0.01 g ascorbyl palmitate, 3.2 g dioleoyl phosphatidyl glycerol and 4.8 g dimyristoyl phosphatidyl choline in a pressure unit and mixed using an overhead stirrer until a clear solution was obtained. Once the solution was clear, 1 g QLT0074 crystals was slowly added under reduced light and mixed using an overhead stirrer until the crystals dissolved completely. The solution was then filtered through a 0.22 µm filter, and tranfered to a round bottom flask. The flask was on a rotary evaporator and the methylene chloride was removed under reduced pressure, with continued drying after the distillation stopped. The vacuum was broken and the flask was attached to a vacuum manifold for further drying. Five hundred mL of sterile filtered 9.2% w/v lactose monohydrate in water for injection was added to the QLT0074/lipid thin film and agitated at room temperature for at least 1h to dissolve and produce multilammelar vesicles. A Model M-1105 microfluidizer was flushed with water then some lactose solution, and then the QLT0074/lipid solution until green solution appeared in the discharge. The following parameters were used: air pressure, 120 psi; operating pressure, 10,030 psi; inlet air pressure gauge reading, 62 psi. The cooling coil reservoir was filled with crushed ice and water to maintain a product temperature in a range of 16–20° C. The QLT/0074 lipid material was processed 5 times through the microfluidizer. The resulting material was then passed through 0.22 µm filters, and aliquoted into labelled lyophilization vials, with 1 ml per aliquot. The material was lyophilized using a BCCA lyophilizer, Labconco, serial # 215369. The lyophilized samples were stored in the dark at 2–8° C.

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

We claim:

1. A composition comprising micelles, said micelles comprising saturated and unsaturated phospholipids and one or more hydro-monobenzo-porphyrin photosensitizer
  wherein the micelles in the composition have an average diameter below about 100 nm.

2. The composition of claim 1 wherein said one or more photosensitizer is BPD-MA, A-EA6, B-EA6 or a combination thereof.

3. The composition of claim 1 wherein one or more of said saturated and unsaturated phospholipids comprise a negatively charged headgroup.

4. The composition of claim 3 wherein said phospholipids comprise DOPG and DMPC.

5. The composition of claim 4 wherein the ratio of DOPG:DMPC is 40:60.

6. The composition of claim 1 wherein said micelles further comprise at least one antioxidant.

7. The composition of claim 6 wherein said at least one antioxidant is butylated hydroxytoluene (BHT) and/or ascorbyl palmitate (AP).

8. The composition of claim 1 wherein the ratio of phospholipids:photosensitizer is 8:1.

9. The composition of claim 2 wherein said photosensitizer is A-EA6 or B-EA6.

10. The composition of claim 1 wherein said micelles have an average diameter below about 50 nm.

11. The composition of claim 10 wherein said micelles have an average diameter below about 30 nm.

12. The composition of claim 11 wherein said micelles have an average diameter below about 20 nm.

13. The composition of claim 1 wherein said unsaturated phospholipid is an egg phospholipid.

14. The composition of claim 1 wherein said unsaturated phospholipid is from a non-animal source.

15. The composition of claim 14 wherein said one or more photosensitizer is BPD-MA, A-EA6 or a combination thereof.

* * * * *

UNITED STATES PATENT AND TRADEMARK OFFICE
CERTIFICATE OF CORRECTION

| | | |
|---|---|---|
| PATENT NO. | : 6,984,395 B2 | |
| APPLICATION NO. | : 09/833406 | |
| DATED | : January 10, 2006 | |
| INVENTOR(S) | : Ronald Erwin Boch et al. | |

It is certified that error appears in the above-identified patent and that said Letters Patent is hereby corrected as shown below:

In the Claims, at column 34, Claim 1, please correct the following:

1. A composition "comprising" --consisting essentially of-- micelles, said micelles comprising saturated and unsaturated phospholipids and one or more hydro-monobenzo-porphyrin photosensitizer
 wherein the micelles in the composition have an average diameter below about 100 nm.

Signed and Sealed this

Seventeenth Day of April, 2007

JON W. DUDAS
*Director of the United States Patent and Trademark Office*